United States Patent [19]

Hashimoto et al.

[11] Patent Number: 4,966,968
[45] Date of Patent: Oct. 30, 1990

[54] INDAN DERIVATIVES

[75] Inventors: Isao Hashimoto, Yamaguchi; Keiichi Yokoyama, Ichihara; Takumi Kitahara, Yamaguchi, all of Japan

[73] Assignee: Mitsui Petrochemical Industries, Ltd., Tokyo, Japan

[21] Appl. No.: 436,805

[22] Filed: Nov. 15, 1989

[30] Foreign Application Priority Data

Nov. 15, 1988 [JP] Japan ................. 63-286706

[51] Int. Cl.$^5$ ................. C07D 295/104; C07D 69/76; C07D 233/11; C07D 235/78
[52] U.S. Cl. ..................... 544/176; 564/169; 560/56
[58] Field of Search ........... 544/176; 564/169; 560/56; 71/82, 107, 108, 118

[56] References Cited

U.S. PATENT DOCUMENTS 4,058,558 11/1977 Cousse et al. .................. 544/176

OTHER PUBLICATIONS

Ruegg et al., Chemical Abstracts, vol. 70(15), entry 68003d (1969).
Ruegg et al., Chemical Abstracts, vol. 72(26), entry 78757h (1970).

Primary Examiner—John M. Ford
Assistant Examiner—Lenora Ava Mittenberger
Attorney, Agent, or Firm—Sherman and Shalloway

[57] ABSTRACT

Discloses indan derivatives represented by the general formula [1]

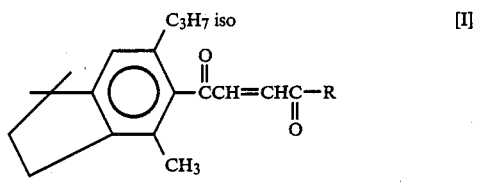

wherein R is a lower alkoxy group, a phenoxy group,

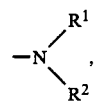

whereupon $R^1$ and $R^2$ are, respectively, a hydrogen atom, a lower alkyl, lower alkenyl, phenyl, or phenyl group substituted by halogen atoms, or a monopholino group.

The indan derivatives demonstrated satisfactory results in respect of a weeding effect and safety in practical use.

10 Claims, No Drawings

INDAN DERIVATIVES

BACKGROUND OF THE INVENTION

The present invention relates to indan derivatives, more particularly, novel indan derivatives which are excellent in a weeding activity.

In recent years, many herbicides have been developed and have contributed to the labor-saving of farming and the improvement of productivity. However, it is hard to say that the herbicides are satisfactory in respect of a weeding effect and safety in practical use. Thus, further improved herbicides have been desired.

The present inventors eagerly studied and researched for development of chemicals which are excellent in a weeding effect, to find out novel indan derivatives bearing specific substituents showing a nigher weeding effect, and arrived at the present invention.

SUMMARY OF THE INVENTION

The present invention provides indan derivatives represented by the following general formula [I]:

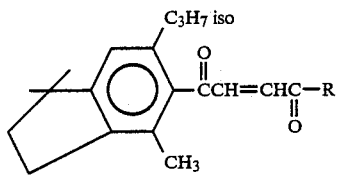

wherein R is a lower alkoxy group, a phenoxy group,

whereupon $R^1$ and $R^2$ are, respectively, a hydrogen atom, a lower alkyl, lower alkenyl, phenyl, or phenyl group substituted by halogen atoms, or $R^1$ and $R^2$ together with the nitrogen atom to which they are bonded form a morpholino group.

DETAILED DESCRIPTION OF THE INVENTION

The indan derivatives of the present invention are represented by the following general formula [I]:

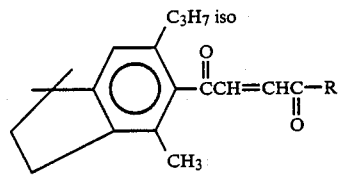

wherein R is a lower alkoxy group, a phenoxy group

whereupon $R^1$ and $R^2$ are, respectively, a hydrogen atom, a lower alkyl, lower alkenyl, phenyl, or phenyl group substituted by halogen atoms, or a morpholino group.

In the formula, the groups represented by R include, as a lower alkoxy group, a methoxy, ethoxy, propoxy, isopropoxy, butoxy, s-butoxy, isobutoxy, t-butoxy, and pentyloxy groups, and the groups represented by $R^1$ and $R^2$, respectively, include, as a lower alkyl group, a methyl, ethyl, propyl, isopropyl, butyl, s-butyl, and isobutyl groups, and as a lower alkenyl group, an allyl and butenyl groups, and as a phenyl group substituted by halogen atoms, a chlorophenyl, dichlorophnyl, trichlorophenyl, fluorophenyl, difluorophenyl, bromophenyl, dibromophenyl, iodophenyl, bromochlorophenyl, and chlorofluorophenyl groups.

Among the compounds of the present invention, the compounds in Table 1, for example, are given as the particularly preferred ones.

TABLE 1

| Compound No. | R | Compound No. | R |
|---|---|---|---|
| 1 | —OCH₃ | 7 | —N(C₂H₅)₂ |
| 2 | —OC₃H₇$^{iso}$ | 8 | —NH(CH₂CH=CH₂) |
| 3 | —OC₄H₉$^s$ | 9 | —NH—C₆H₅ |
| 4 | —O—C₆H₅ | 10 | —NH—C₆H₃Cl₂ |
| 5 | —NH₂ | 11 | —NH—C₆H₃Cl₂ |
| 6 | —NHCH₃ | 12 | —N(morpholino) |

[Synthesis of Indan Derivatives]

The indan derivatives of the present invention could be synthesized according to the following reaction formulae (1) to (3).

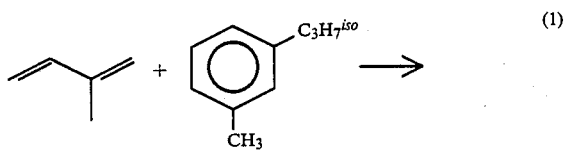

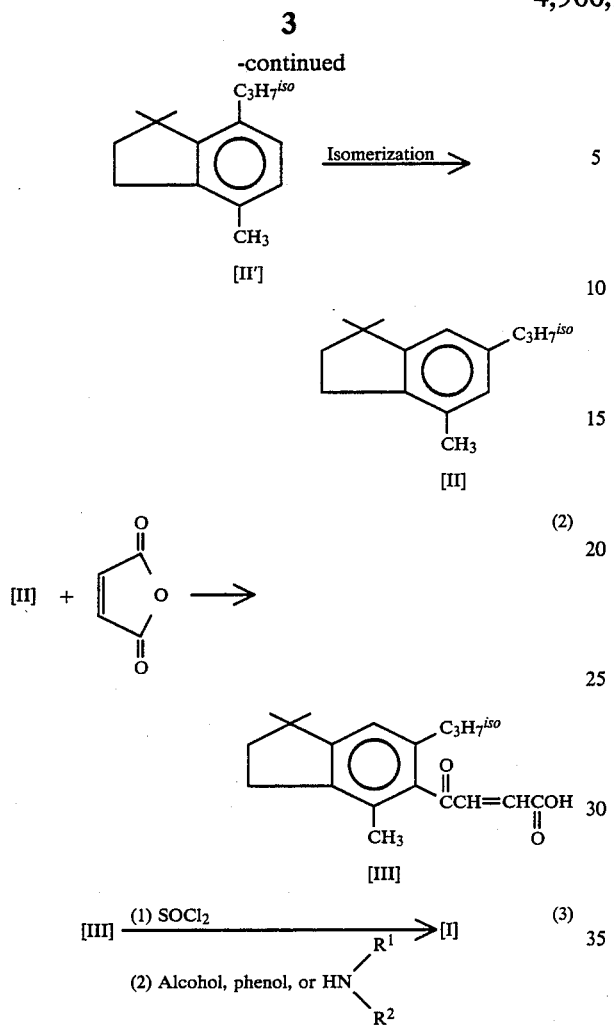

added 20 ml of methylene chloride, 10.0 g (33 m mole) of 3-(1,1-dimethyl-6-isopropyl-4-methyl-5-indanoyl) acrylic acid (the compound of the formula III), and 2.5 ml (33 m mole) of thionyl chloride at room temperature, followed by reaction under reflux for 2 hrs., to obtain a methylene chloride solution of acid chloride therefrom. To this was added the mixture of 10 ml of methanol and 10 ml of pyridine at −20° C, followed by being stirred for 1 hr at −20 to −10° C. The reaction mixture was poured into 100 ml of water, and was then extracted with 200 ml of ether.

The ether layer was washed with 0.5 N HCl and dried by sodium sulfate. Following removal of the ether, the product was subjected to vacuum distillation, to obtain 6.3 g (yield: 60%) of the objective product in the form of a yellow crystal (m.p.: 88° to 89° C.), from the fractions of b.p. 160° to 163° C./1.6 mmHg.

NMR spectrum (CDCl$_3$) $\delta$1.17 (d,6H,J=7H$_z$) 1.25(s,6H), 1.92(t, 2H,J=7H$_z$), 2.04(s.3H), 2.66 (sept., 1H, J =7H$_z$)m 2.77 (t,2H, J=7H$_z$), 3.78 (s,3H), 6.38 (d,1H, J=16H$_z$), 6.94 (s,1H), 7.22 (d, 1H, J=16H$_z$)

Synthesis Example 2

Synthesis of 3-(1,1-dimethyl-6-isopropyl-4-methyl-5-indanoyl)-acryl amide (Compound No. 5)

The reaction was performed in the same manner as those disclosed in Synthesis Example 1 except that 15 ml of 25% aqueous ammonia was added in place of 10 ml of methanol and 10 ml of pyridine. The resultant impure crystals were recrystalized from ethyl acetate - toluene, to obtain the objective product with 70% yield (yellow powder with m.p. of 235° to 237° C.).

NMR spectrum (CDCl$_3$) $\delta$1.15 (d,6H, J=7.5H$_z$), 1.24 (s, 6H), 1.89 (t, 2H, J=7.5H$_z$), 2.01 (s, 3H), 2.63 (sept. ,1H, J=7H$_z$), 2.76 (t, 2H, J=7.5H$_z$), 6.52 (d,$_1$H, J=17H$_z$), 6.94 (s, 1H), 7.06(d, 1H, J=17H$_z$), 7.14(s,1H), 7.84(s,1H)

Synthesis Examples 3 to 10

The compounds in Table 2 were synthesized in the same manner as those disclosed in Synthesis Example 1 or 2.

The reaction (1) proceeds easily at 0 to 30° C. under a solventless condition or in a solvent, such as halogenated hydrocarbons, in the presence of an acid catalyst, such as sulfuric acid, and aluminium chloride, etc. The reaction (2) proceeds easily at 0° to 40° C. in an inert solvent, such as halogenated hydrocarbons, in the presence of a Lewis acid, such as aluminium chloride, etc.

Among the indan derivatives of the present invention, the esters, i.e. the derivatives in which R is a lower alkoxy group, or a phenoxy group, can be synthesized by reaction of acid chloride obtained from carboxylic acid [III] and equimolar thionyl chloride with corresponding ROH, i.e. alcohols or phenol, in the presence of a base, i.e. such as triethylamine, pyridine, etc. Among the indan derivatives of the present invention, the amides, i.e. the derivatives in which R is —N(—R$^1$-)—R$^2$, whereupon R$^1$ and R$^2$ are the same as those already defined, or R is a morpholino group, can be synthesized by reaction of the above-described acid chloride with the corresponding amines with molar ratio of the former to the latter of 1:2 to 10 in the reaction.

In the below, the syntheses will be explained definitely with referring to synthesis examples.

Synthesis Example 1

Synthesis of methyl 3-(1,1-dimethyl-6-isopropyl-4-methyl-5-indanoyl)acrylate (Compound No. 1)

To a 100 ml flask equipped with a thermometer, a reflux condenser, a dropping funnel, and a stirrer, were

TABLE 2

| Compound No. | Yield (%) | mp (°C.) | Spectrum data |
|---|---|---|---|
| 2 | 80 | 69~71 | NMR (CDCl$_3$) $\delta$1.17(d, 6H, J=7Hz), 1.24(s, 6H), 1.26(d, 6H, J=5Hz), 1.90(t, 2H, J=7Hz), 2.03(s, 3H), 2.68(m, 1H), 2.75 (t, 2H, J=7Hz), 5.07(sept., 1H, J=7 Hz), 6.32(d, 1H, J=16Hz), 6.94(s, 1H), 7.20(d, 1H, J=16Hz) |
| 3 | 76 | 65~67 | |
| 4 | 90 | Liquid | IR (neat, $\nu$ c=o)1740, 1660 cm$^{-1}$ |
| 7 | 81 | 50~52 | NMR (CDCl$_3$) $\delta$1.13(t, 6H, J=7Hz), 1.20(d, 6H, J=7Hz), 1.25(s, 6H), 1.91(t, 2H, J=7Hz), 2.07(s, 3H), 2.77(t, 2H, J=7Hz), 3.30(q, 2H, J=7Hz), 3.44(q, 2H, J=7Hz), 6.92(d, 1H, J=16Hz), 6.97 (s, 1H), 7.17(d, 1H, J=16Hz) |
| 9 | 90 | 184~186 | IR (KBr Disk $\nu$ c=o) 1653 cm$^{-1}$ |
| 10 | 67 | 235~236 | NMR (CDCl$_3$/DMSO-d$_6$) $\delta$1.19(d, 6H, J=8Hz), 1.25(s, 6H), 1.91 (t, 2H, J=8Hz), 2.06(s, 3H), 2.70(m, 1H), 2.78(t, 2H, J=8Hz), 6.74 (d, 1H, J=16Hz), 6.97(s, 1H), 7.28 (d, 1H, J=16Hz), 7.29(d, 1H, J=10Hz), 7.50(d, 2H, J=10Hz), 7.94 (s, 1H) |
| 11 | 80 | 225~227 | IR (KBr Disk $\nu$ c=o) 1689, |

TABLE 2-continued

| Compound No. | Yield (%) | mp (°C.) | Spectrum data |
|---|---|---|---|
| 12 | 86 | 149~150 | 1638 cm$^{-1}$ IR (KBr Disk $\nu$ c=o) 1673, 1637 cm$^{-1}$ |

The indan derivatives relating to the present invention show a higher weeding effect on many kinds of annual broad-and narrow-leaved weeds in a paddy field or an upland field.

In order to employ the compounds of the present invention as a herbicide, the present compound is sprayed after being diluted to a suitable concentration or directly applied, solely, or in the form of chemicals, such as wettable powder, emulsion, fine powder, granules, or the like, into which a carrier, a surface-active agent, a dispersing agent, an adjuvant, or the like, is compounded.

For use, the compounds of the present invention, or chemicals containing said compounds, not only can be sprayed on crops directly, but also can mixed in soil.

The applied amounts differ depending on the type and the degree of objective weeds and damages, the type of crops, and the application mode. For use as an usual herbicide, however, the effective amounts are about 1 to 100 g per are.

Following are compounding examples for chemicals, in which the present compounds are employed as an active ingredient. In the following disclosure, "percent" means weight percent, and "parts" means weight parts.

Compounding Example 1 (Wettable powder)

The compound of the present invention, sodium salt of higher alcohol sulfate, and kaoline whose compounding ratio was 10:3:87 by percent, respectively, were mixed and grained, to produce wettable powder.

Compounding Example 2 (Emulsion)

The compound of the present invention, polyoxyethylene alkyl arylether, cyclohexanone, and dimethylformamide were dissolved uniformly in the compounding ratio of 20:10:30:40 by percent, respectively, to produce emulsion.

Compounding Example 3 (Granules)

The compound of the present invention, bentonite, and clay whose compounding ratio was 5:40:50:5 by percent, respectively, were mixed and grained uniformly. Following addition of water thereto and milling, the resultant product was formed into granules and dried, to produce granules.

Compounding Example 4 (Fine powder)

The compound of the present invention was mixed with clay, and then grained uniformly in the compounding ratio of 3 to 97 by percent, respectively, to produce fine powder.

Next, the weeding effect by the present compounds will be explained with referring to test examples.

Test Examples 1 to 10

Two sheets of filter papers were put in a 9 cm diameter laboratory dish with a cap, and seeds of *Echinochloa crus-galli, Digitaria adscendens, Cyperus iria L., Scirpus juncoides subsp.*, and *Amaranthus viridis*, were put on the filter papers. 20 ml of liquid fertilizer and a test compound (wettable powder) was given after dilution with water, so as to be sprayed thereupon in a proportion of 100 g/10 ares as an active ingredient. After exposed to light (3,000 luxes) for 10 days at 30, the weeding effects were evaluated visually based on the standards in Table 3.

TABLE 3

| Index | Weeding effect |
|---|---|
| 5 | |
| 4.5 | 90% to 99% |
| 4 | 80% to 89% |
| 3.5 | 70% to 79% |
| 3 | 60% to 69% |
| 2.5 | 50% to 59% |
| 2 | 40% to 49% |
| 1.5 | 30% to 39% |
| 1 | 20% to 29% |
| 0.5 | 19% to 1% |
| 0 | none |

Results are shown in Table 4.

TABLE 4

| Tested Compound (Compound No.) | Weeding Effect | | | | |
|---|---|---|---|---|---|
| | *Echinochloa crusgalli* | *Digitaria adscendens* | *Cyperus iria L.* | *Scripus juncoides* subsp. | *Amaranthus viridis* |
| 1 | 4 | 4 | 5 | 4 | 5 |
| 2 | 3 | 3 | 4 | 3 | 5 |
| 3 | 3 | 2.5 | 4 | 3 | 4 |
| 4 | 4 | 4 | 5 | 4 | 5 |
| 5 | 5 | 5 | 5 | 4 | 5 |
| 7 | 5 | 3 | 4.5 | 4 | 4.5 |
| 9 | 2 | 5 | 4 | 3 | 3 |
| 10 | 4 | 3 | 3 | 3 | 4 |
| 11 | 4 | 4 | 5 | 3 | 4 |
| 12 | 4 | 4.5 | 5 | 4 | 5 |
| Comparative Compound* | 1 | 0 | 0 | 0 | 1 |

*3-(1,1-dimethyl-6-isopropyl-4-methyl-5-indanoyl)acrylic acid represented by the formula:

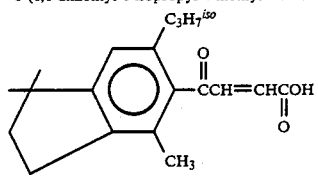

What is claimed is:

1. Indan derivatives represented by the formula (I):

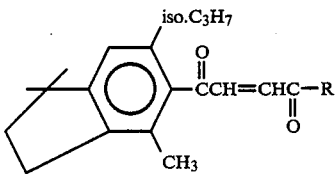 (I)

wherein R is a lower alkoxy group, a phenoxy group,

whereupon $R^1$ and $R^2$ are respectively, a hydrogen atom, a lower alkyl, lower alkenyl, phenyl, or phenyl group substituted by halogen atoms, or $R^1$ and $R^2$ together with the nitrogen atom to which they are bonded form a morpholino group.

2. An indan derivative as claimed in claim 1, wherein R is methoxy.
3. An indan derivative as claimed in claim 1, wherein R is isopropoxy.
4. An indan derivative as claimed in claim 1, wherein R is sec. butoxy.
5. An indan derivative as claimed in claim 1, wherein R is phenoxy.
6. An indan derivative as claimed in claim 1, wherein R is amino.
7. An indan derivative as claimed in claim 1, wherein R is diethylamino.
8. An indan derivative as claimed in claim 1, wherein R is phenylamino.
9. An indan derivative as claimed in claim 1, wherein R is dichlorophenylamino.
10. An indan derivative as claimed in claim 1, wherein R is morpholino.

* * * * *